(12) United States Patent
Pruter

(10) Patent No.: US 7,452,331 B1
(45) Date of Patent: Nov. 18, 2008

(54) VASCULAR ADJUSTABLE MULTI-GAUGE TILT-OUT METHOD AND APPARATUS FOR GUIDING NEEDLES

(76) Inventor: Rick L Pruter, 21 Woodcrest La. NE., Iowa City, IA (US) 52240

( * ) Notice: Subject to any disclaimer, the term of this patent is extended or adjusted under 35 U.S.C. 154(b) by 459 days.

(21) Appl. No.: 10/906,061

(22) Filed: Feb. 1, 2005

Related U.S. Application Data

(63) Continuation-in-part of application No. 10/250,149, filed on Jun. 6, 2003, now Pat. No. 7,087,024, which is a continuation of application No. 09/682,367, filed on Aug. 24, 2001, now Pat. No. 6,612,990, which is a continuation-in-part of application No. 09/526,048, filed on Mar. 15, 2000, now Pat. No. 6,296,614, which is a continuation-in-part of application No. 29/103,098, filed on Apr. 8, 1999, now Pat. No. Des. 424,693.

(51) Int. Cl.
*A61B 8/00* (2006.01)
(52) U.S. Cl. .............. 600/461; 600/462; 600/466; 600/433; 600/434; 600/585
(58) Field of Classification Search .......... 600/585, 600/461, 463, 433, 434, 466, 462
See application file for complete search history.

(56) References Cited

U.S. PATENT DOCUMENTS

| | | | |
|---|---|---|---|
| 2,451,183 A | 10/1948 | Tantimonaco | |
| 2,536,963 A | 1/1951 | Stephens | |
| 3,017,887 A | 1/1962 | Heyer | |
| 3,538,915 A | 11/1970 | Frampton et al. | |
| 3,556,079 A | 1/1971 | Omizo | |
| 4,029,084 A | 6/1977 | Soldner | |
| 4,058,114 A | 11/1977 | Soldner | |
| 4,108,165 A | 8/1978 | Kopp et al. | |
| 4,132,496 A | 1/1979 | Casto | |
| 4,249,539 A | 2/1981 | Vilkomerson et al. | |
| 4,289,139 A | 9/1981 | Enjoji et al. | |
| 4,332,248 A | 6/1982 | DeVitis | |
| 4,363,326 A | 12/1982 | Kopel | |
| 4,402,324 A | 9/1983 | Lindgren et al. | |
| 4,408,611 A | 10/1983 | Enjoji | |
| 4,469,106 A | 9/1984 | Harui | |
| 4,489,730 A | 12/1984 | Jingu | |
| 4,491,137 A | 1/1985 | Jingu | |
| 4,497,325 A | 2/1985 | Wedel | |
| 4,504,269 A | 3/1985 | Durand | |
| 4,542,747 A | 9/1985 | Zurinski et al. | |

(Continued)

OTHER PUBLICATIONS

"ultrasoundsupplies.com" brochure of Civco Medical Instruments Co.

(Continued)

*Primary Examiner*—Brian L. Casler
*Assistant Examiner*—John F Ramirez
(74) *Attorney, Agent, or Firm*—Simmons Perrine PLC

(57) ABSTRACT

An apparatus and method for guiding a needle in conjunction with a biopsy using a medical imaging device, where an open-ended needle guide with an adjustable pivoting multi-gauge needle stop is used to guide a needle during insertion and during a tilting of the needle with respect to the medical imaging device.

10 Claims, 5 Drawing Sheets

U.S. PATENT DOCUMENTS

| | | | |
|---|---|---|---|
| 4,576,175 A * | 3/1986 | Epstein | 600/461 |
| 4,635,644 A | 1/1987 | Yagata | |
| 4,781,067 A | 11/1988 | Cichanski | |
| 4,898,178 A | 2/1990 | Wedel | |
| 4,899,756 A | 2/1990 | Sonek | |
| 4,970,907 A | 11/1990 | Flynn | |
| 5,052,396 A | 10/1991 | Wedel et al. | |
| 5,076,279 A | 12/1991 | Arenson et al. | |
| 5,088,500 A | 2/1992 | Wedel et al. | |
| 5,095,911 A * | 3/1992 | Pomeranz | 600/463 |
| 5,161,764 A | 11/1992 | Roney | |
| 5,235,987 A | 8/1993 | Wolfe | |
| 5,343,865 A | 9/1994 | Gardineer et al. | |
| D362,064 S | 9/1995 | Smick | |
| 5,623,931 A | 4/1997 | Wung et al. | |
| D383,968 S | 9/1997 | Bidwell et al. | |
| 5,758,650 A | 6/1998 | Miller et al. | |
| 5,871,448 A | 2/1999 | Ellard | |
| 5,910,113 A | 6/1999 | Pruter | |
| 5,924,992 A | 7/1999 | Park et al. | |
| 5,941,889 A | 8/1999 | Cermak | |
| D424,693 S | 5/2000 | Pruter | |
| 6,139,544 A | 10/2000 | Mikus et al. | |
| 6,203,499 B1 | 3/2001 | Imling et al. | |
| 6,238,336 B1 | 5/2001 | Ouchi | |
| 6,296,614 B1 * | 10/2001 | Pruter | 600/461 |
| 6,311,084 B1 | 10/2001 | Cormack et al. | |
| 6,361,499 B1 * | 3/2002 | Bates et al. | 600/461 |
| 6,379,307 B1 | 4/2002 | Filly et al. | |
| 6,612,990 B1 | 9/2003 | Pruter | |
| 6,758,817 B1 * | 7/2004 | Pruter et al. | 600/461 |
| 6,796,948 B2 * | 9/2004 | Kanesaka | 600/585 |

OTHER PUBLICATIONS

"Endocavity Needle Guide Kits" brochure of Civco Medical Instruments, © 2000, Solutions for Imaging.

"General Purpose Needle Guides and Transducer Covers" brochure of Civco Medical Instruments, SONOSITE Cross-Reference Information.

"Needle Guidance Systems, Transducer Covers, GE Medical Systems", gemedicalsystems.com brochure of Civco Medical Instruments, Solutions for Imaging.

UltraGuide 1000 System 4-page brochure, UltraGuide Ltd., Tirat Hacarmel Industrial Park, P O Box 2070, Tirat Hacarmel 30200, Israel.

UltraGuide 1000 2-page brochure, UltraGuide Ltd., Tirat Hacarmel Industrial Park, P O Box 2070, Tirat Hacarmel 30200, Israel.

"Civcoscan, Product News and Special Offers From Civco" Brochure of Civco Medical Instruments, Winter 2001.

Solutions for Ultrasound, Civco Medical Instruments Co., Inc., Medical Parkway, 102 Highway 1 South, Kalona, IA 52247.

Program for Medical Ultrasound Professionals, Winter 1995, Civco Medical Instrument Co., Inc., Medical Parkway, 102 Highway 1 South, Kalona, IA 52247.

Disposable Transrectal Needle Guide, Civco Medical Instruments Co., Inc., Medical Parkway, 102 Highway 1 South, Kalona, IA 52247.

Maggi & Maggi II Plus, Sterile General Purpose Biopsy Needle Guides, Civco Medical Instrument Co., Inc., Medical Parkway, 102 Highway 1 South, Kalona, IA 52247.

Ultra-Pro Sterile General Purpose Biopsy Needle Guide, Civco Medical Instruments Co., Inc., Medical Parkway, 102 Highway 1 South, Kalona, IA 52247.

Aloka Needle Guide/Probe Cover Kits, Civco Medical Instruments Co., Inc., Medical Parkway, 102 Highway 1 South, Kalona IA 52247.

Multi Pro 2000, Multi-Purpose Ultrasound Linear Tracking Instrument, Civco Medical Instruments Co., Inc., 418 B Avenue, Kalona, IA 52247.

"The Ultimate Guide in Ultrasound" advertising, Civco Medical Instruments Co., Inc., 418 B Avenue, Kalona, IA 52247.

"Hitting the Mark with Realtime Guidance", Civco PROgram, Drawer Q, Kalona, IA 52247.

"Dedicated Breast Ultrasound, USI Introduces A Revolution In Breast Ultrasound . . . Vista" by USI The Breast Imaging Company. Three-page web page of amedic.se printed on Nov. 5, 2002.

Affidavit of Applicant Admitted prior art dated Jun. 27, 2003. Toshiba Product Description UAGV021A.

* cited by examiner

VASCULAR ADJUSTABLE MULTI-GAUGE TILT-OUT METHOD AND APPARATUS FOR GUIDING NEEDLES

CROSS-REFERENCE TO RELATED APPLICATIONS

The present invention is a continuation-in-part application of co-pending application entitled "Method and Apparatus for Guiding Needles" by the same inventor, the application having Ser. No. 10/250,149 filed on Jun. 6, 2003, which is a continuation of application Ser. No. 09/682,367 entitled "Method and apparatus for guiding needles", filed by the same inventor on Aug. 24, 2001, which application has now issued as U.S. Pat. No. 6,612,990, and which itself was based upon a continuation-in-part application of an application entitled "Needle guide for attachment to ultrasound transducer probe" by the same inventor, the application having Ser. No. 09/526,048, which was filed on Mar. 15, 2000, and issued as U.S. Pat. No. 6,296,614 on Oct. 2, 2001, which itself was a continuation-in-part of application 29/103,098, also entitled "Needle guide for attachment to ultrasound transducer probe" filed on Apr. 8, 1999, which issued as U.S. Pat. No. Des. 424,693 on May 9, 2000. The above-referenced applications, patents and U.S. Design patent are incorporated herein in their entirety by these references.

FIELD OF THE INVENTION

The present invention generally relates to needle guides for medical imaging transceivers, and more particularly relates to needle guides for medical imaging transceivers which permit tipping of a needle while still in the needle guide.

BACKGROUND OF THE INVENTION

In recent years, handheld medical imaging transceivers, such as ultrasound and gamma ray transceivers, have been used extensively for various medical imaging situations. In certain procedures, such as biopsies, it may be desired to tilt a needle with respect to a needle guide or vice versa.

In the past, the physician or medical professional may be required to detach a biopsy needle from a needle guide prior to changing the angle of the needle with respect to the needle guide and transceiver. Other prior art needle guides have included a pair of spaced-apart fixed parallel plates. The medical professional could place the needle between the parallel plates, and it would be free in a plane parallel with the plates, but restricted from large movements outside that plane.

Other prior art needle guides have been used which include a resilient tube coupled to a transducer where the tube has a longitudinal slit through which the needle can be pulled when relative tilting is required.

While these needle guides have been used extensively in the past, they do have some drawbacks. First of all, any model of fixed parallel plate needle guide is limited in the size of needle that can be guided therein. If the needle is too big, it will not fit between the fixed parallel plates. If the plates are too far apart, there is less support being provided in the desired direction. Also, these parallel plate needle guides only provide support in one direction. They provide no support or resistance from motion within the plane of the parallel gap between the fixed plates. This increases the attention required by the medical professional.

Secondly, the resilient slit tube type of needle guide does provide some resistance to motion in the desired plane of motion, but it is limited to only the first portion of that movement or motion. Once the needle is tilted out of the tube, there is no support or resistance to motion in any direction. Additionally, these types of needle guides will work only with specific gauges of needles. They will not work well when a narrow gauge needle is used in a needle guide primarily designed for a larger needle. The narrower needle may fall through the slit. Conversely, a larger needle may not fit in the tube, or it may be difficult to pull through the slit. Consequently, numerous sized slit tube needle guides would be needed to fulfill the needs of a medical professional who uses needles of varying sizes. Additionally, these slit tube type of needle guides may be viewed as unstable in the direction of relative motion. For example, the force required to be applied to the needle to move the needle in the tilted direction decreases as the amount of tilting occurs. To assure that excess tilting does not occur, the medical professional needs to give more attention to the force being applied when the required force decreases with angular displacement.

Consequently, there exists a need for improved methods and apparatus for guiding needles in an efficient manner.

SUMMARY OF THE INVENTION

It is an object of the present invention to provide an apparatus and method for guiding a tiltable needle in an efficient manner.

It is a feature of the present invention to utilize a multi-gauge adjustable needle guide.

It is another feature of the present invention to include a slidable needle stop.

It is another feature of the present invention to include a slidably adjustable needle guide stop with a bias force for closing the needle guide.

It is another feature of the present invention to include needle stops having contours for engaging needles.

It is yet another feature of the present invention to provide a pivoting needle stop.

It is still another feature of the present invention to provide a pivoting needle stop with a beveled needle engaging surface.

It is an advantage of the present invention to achieve improved efficiency in guiding needles.

The present invention is an apparatus and method for guiding needles designed to satisfy the aforementioned needs, provide the previously stated objects, include the above-listed features, and achieve the already articulated advantages. The present invention is carried out in a "physician burden-less" manner in a sense that the burden on a physician or other medical professional in guiding needles during the process of tilting has been greatly reduced.

The present invention is also carried out in an inexpensive and durable way by avoiding the need to utilize a sliding mechanism and a spring.

Accordingly, the present invention is an apparatus and method including in one embodiment a slidable needle stop in a multi-gauge adjustable needle guide and in another embodiment, a pivoting needle stop.

BRIEF DESCRIPTION OF THE DRAWINGS

The invention may be more fully understood by reading the following description of the preferred embodiments of the invention, in conjunction with the appended drawings wherein.

DETAILED DESCRIPTION

Figure 1:
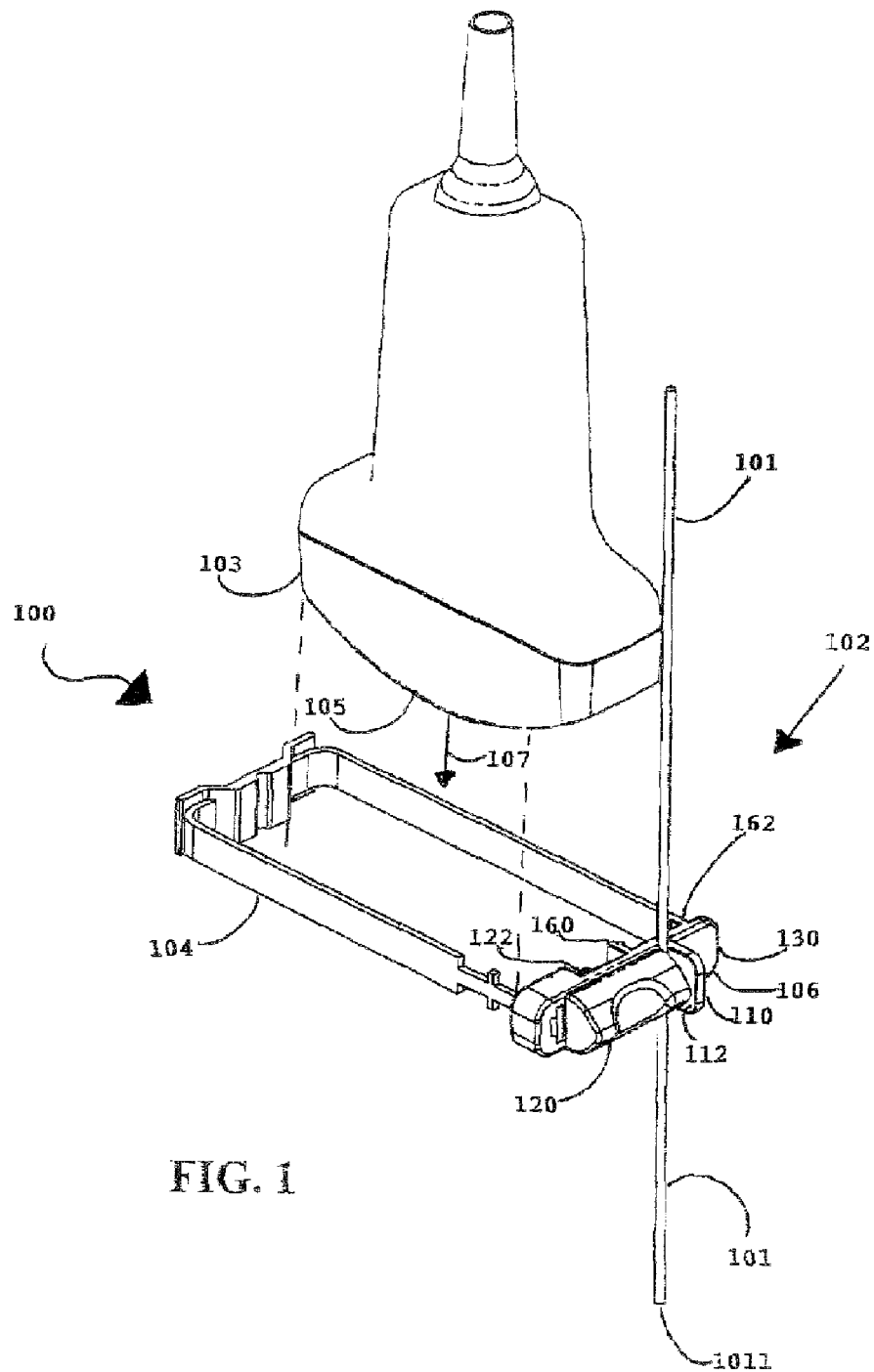
FIG. 1 is a partially exploded perspective view of the apparatus of the present invention.

Now referring to the drawings wherein like numerals refer to like matter throughout, and more specifically referring to FIG. 1, there is shown a needle guide assembly 100 of the present invention which includes a needle guide 102 with a needle 101 disposed therein. Needle guide 102 is coupled to medical imaging device 103, which could be an ultrasound transducer, gamma ray transceiver or other imaging device, via a medical imaging device retaining strap 104, which could be an elastic strap, such as rubber or a less elastic strap, such as fabric or leather. Cables, wires, rope, brackets, clamps or any other suitable substitute could be used for a medical imaging device retaining strap 104. Needle guide 102 is preferably a plastic material, such as ABS or equivalent; however, other materials, such as aluminum, surgical steel, and any other suitable material could be substituted.

The medical imaging device 103 has a transmitting end 105, which may be a planar face with a vertical axis 107 extending orthogonally therefrom.

The term "vertical axis 107" is used herein to convey that the axis is orthogonal to the transmitting surface end 105. Depending on the orientation of the medical imaging device 103, the vertical axis 107 may be pointed in any direction with respect to the patient or an earth reference. In normal operation, the medical imaging device 103 is often held, at least at first, with the transmitting end 105 in a substantially horizontal (earth reference) arrangement. This arrangement results in the vertical axis 107 being orientated in a vertical (earth reference) direction.

Needle guide 102 has a slidable needle stop 120 which may be contoured on its top side to facilitate engagement with a human finger or thumb. Slidable needle stop 120 is preferably slidable along needle guide main body 106, which contains a first needle stop 110. However, other arrangements between the slidable needle stop 120 and first needle stop 110 could be substituted. First needle stop 110 may be vertical and have a planar needle engagement surface 112 as shown, but other arrangements could be employed as well.

Also shown in FIG. 1 are members 160 and 162, which can form a pliable clip for attaching needle guide 102 to a bracket (not shown) coupled to a medical imaging transceiver when strap 104 is not used.

Figure 2:
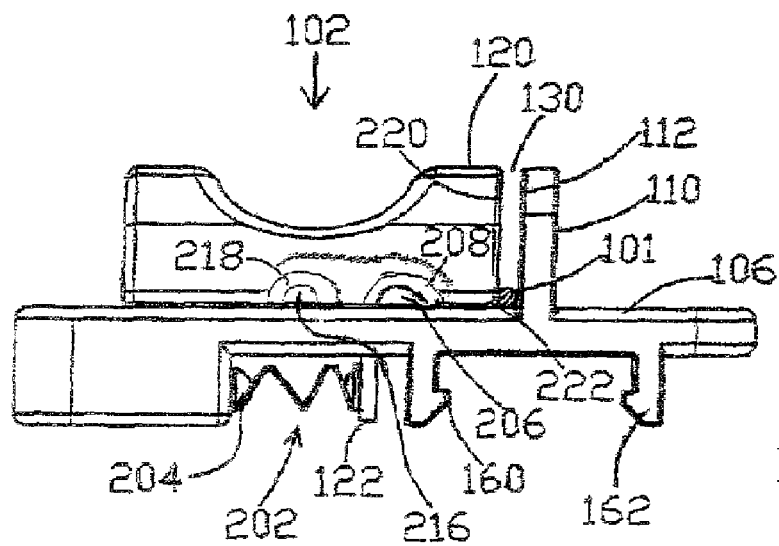
FIG. 2 is an enlarged partially cut-away side view of the needle guide of FIG. 1, where the cut-away portion exposes a plurality of detent mechanisms.

Now referring to FIG. 2, there is shown a partially cut-away side view of the needle guide 102 of FIG. 1. Needle guide 102 is shown having a spring 202, which could be a simple metal or plastic spring, or it could be any resilient member or other apparatus capable of biasing sliding spring stop 122 so as to tend to minimize the width of needle gap 130. Spring 202 is shown disposed between fixed spring stop 204 and sliding spring stop 122. Needle guide 102 is also shown in the cut-away portion as having a needle guide main body 106, first detent protrusion 206 and second detent protrusion 216 which are received by first detent protrusion receiving void 208 and second detent protrusion receiving void 218 both found in slidable needle stop 120. Slidable needle stop 120 is shown having a top leading edge 220 and a bottom angled leading edge 222. Preferably, the pressure exerted by spring 202 is sufficient to hold needle 101 stationary unless a force other than gravity acts upon it.

Figure 3:
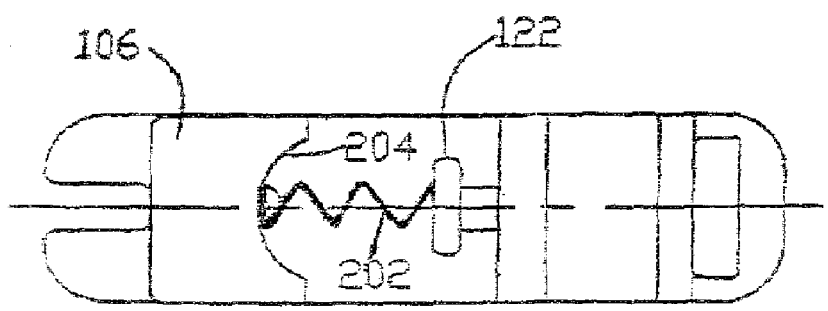
FIG. 3 is a bottom view of the needle guide of FIGS. 1 and 2.

Now referring to FIG. 3, there is shown a bottom view of the needle guide 102 of FIGS. 1 and 2.

In operation, the apparatus and method of the present invention as described and shown in FIGS. 1-3, could function as follows:

Needle guide 102 is attached to medical imaging device 103 via medical imaging device retaining strap 104. The needle guide 102 is readied for receipt of the needle 101 by sliding slidable needle stop 120 to create a gap sufficiently large to accommodate the particular biopsy needle used. The biopsy needle, such as needle 101, is inserted into needle gap 130, and slidable needle stop 120 is released, thereby holding needle 101. The needle 101 is then inserted into the patient. Medical imaging device 103 is used to create a first image of a portion of a human body. The medical imaging device 103 and needle guide 102 are then tilted with respect to the needle 101. This provides a different angle of view of the end 1011 of the needle 101. A second image is then created by the medical imaging device 103. The needle may be held stationary and the medical imaging device 103 and needle guide 102 tilted, or vice versa.

The tilting of the needle 101 or needle guide 102 is done by applying a force between the two. As the angle of separation between the vertical axis 107 and the longitudinal axis of the needle 101 increases, the amount of contact between the needle 101 and planar needle engagement surface 112 and top leading edge 220 increases. This increases the friction on the needle 101, thereby increasing the force needed to move the needle 101 to larger angular separations with respect to the needle guide 102.

Figure 4:
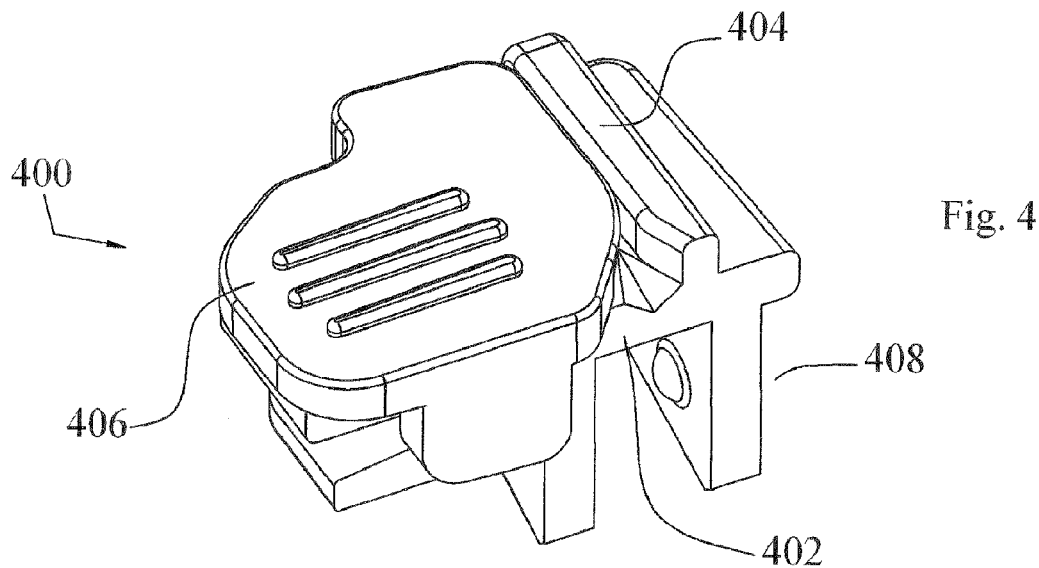
FIG. 4 is a perspective view of a top portion of the present invention having a pivoting needle stop.

Now referring to FIG. 4, there is shown a vascular adjustable multi-gauge tip-out needle guide generally designated 400, having a base region 402, a stationary needle engaging member 404, and a pivoting needle engaging member 406. FIG. 4 shows the top side of the needle guide 400 and an angled end of the stationary needle engaging member 404 so as to facilitate insertion of a needle into a void between the members 404 and 406. Also shown is a mechanism 408 for coupling the needle guide 400 to an imaging transceiver, bracket or other structure. Mechanism 408 is shown as resilient member or plurality of members which are made to mate with a bracket or mating portion of an imagining transceiver or other medical instrument.

Figure 5:
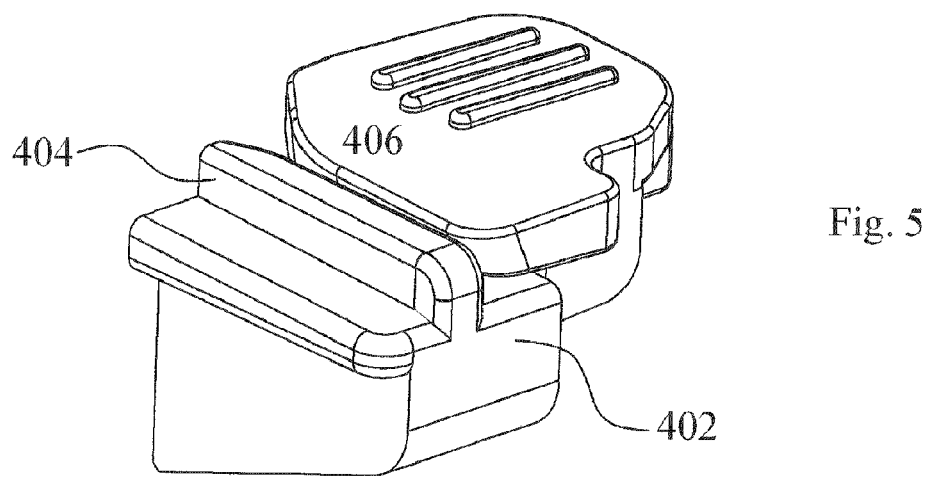
FIG. 5 is a perspective view of a bottom portion of the needle guide of FIG. 4.

FIG. 5 shows a needle guide 400 of FIG. 4 from a view to show the bottom.

Figure 6:
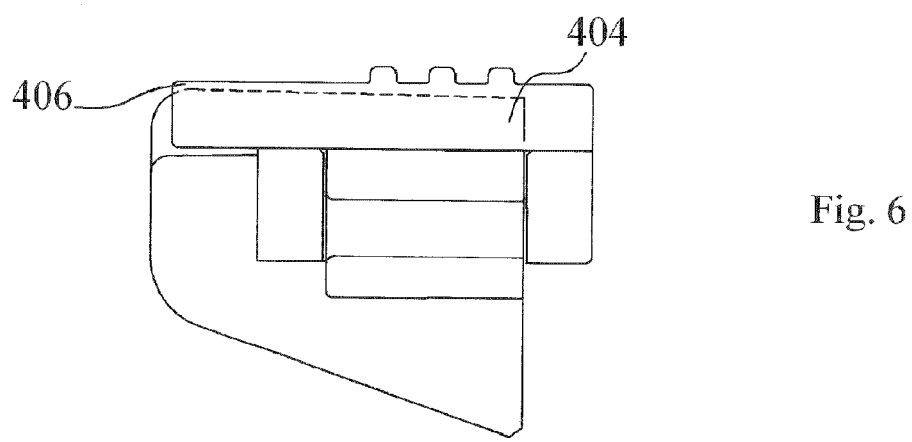
FIG. 6 is an elevation view of the needle guide of FIG. 4.

FIG. 6 shows an elevation view of an end of the needle guide 400 where the edge of the member 406 is in the foreground and the top portion of the member 404 is in the background.

Figure 7:
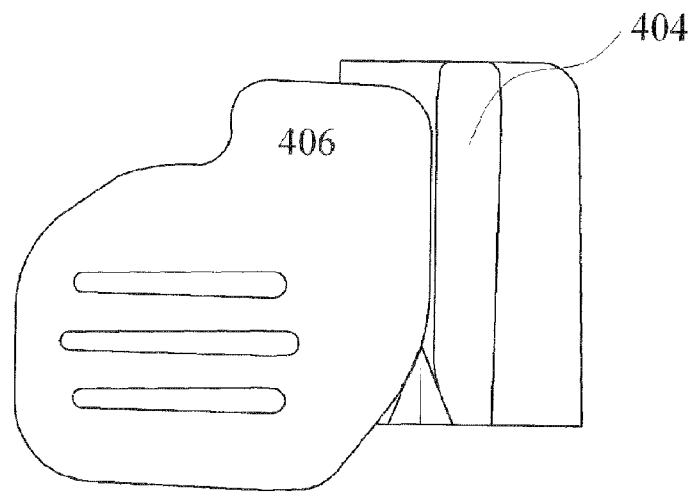
FIG. 7 is a plan view of the needle guide of FIG. 4.

FIG. 7 is a plan view of the needle guide 400.

Figure 8:
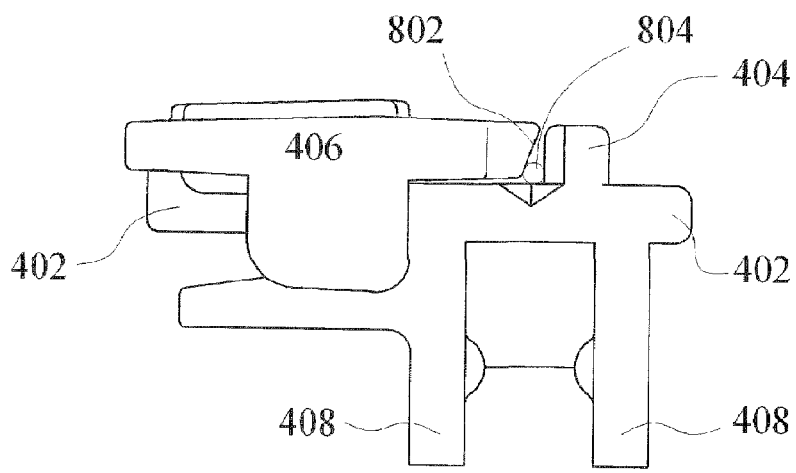
FIG. 8 is an elevation view of the needle guide of FIG. 4 showing the pivoting needle stop in contact with a needle 804.

FIG. 8 is an elevation view of the needle guide 400 where the beveled edge 802 of the pivoting member 406 is shown engaging the needle 804.

Figure 9:
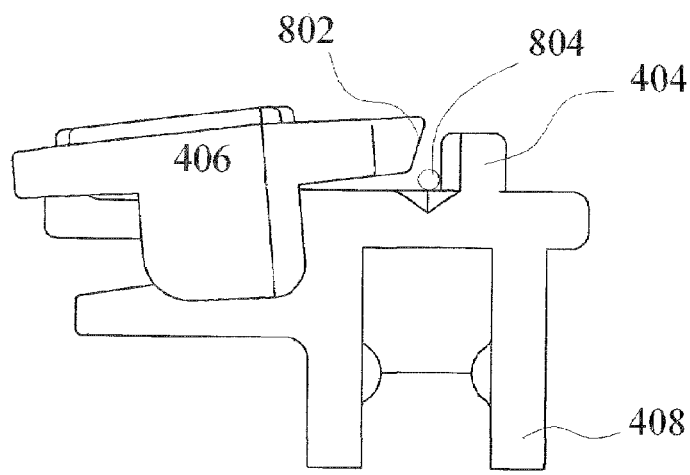
FIG. 9 is an elevation view of the needle guide of FIG. 8 wherein the needle stop has been pivoted away to accommodate a larger needle 902. The smaller gauge needle 804 of FIG. 8 is also shown to aid in the understanding of how the needle guide 400 operates. It should be understood that the smaller gauge needle 804 and the larger gauge needle 902 would not be simultaneously disposed as shown.

Now referring to FIG. 9, it can be seen that the needle 804 can be tipped out from the needle guide 400 by depressing the member 406, causing it to pivot and thereby increase the gap between the beveled edge 802 and the stationary member 404. Once the pivoting member is pivoted sufficiently, the needle can be tipped out with little resistance. The needle also could be tipped out without manually pressing a distal end of the pivoting member if the needle itself applies enough force to the beveled edge so as to cause the pivoting member to move. If a one-handed operation is desired, then the resistance or bias of the pivoting member to return to a minimized needle gap could be designed to permit relatively easy pivoting of the pivoting member without exceeding a limit of pressure to be applied by the needle.

Figure 10:
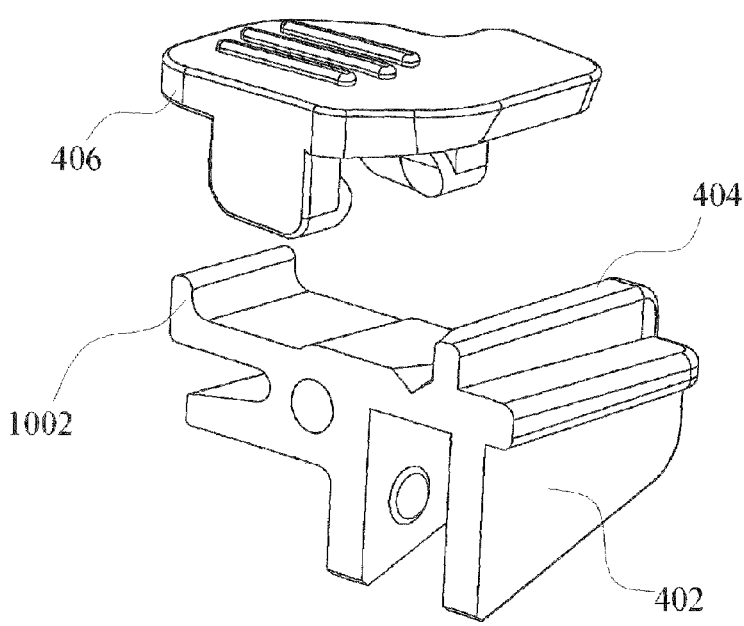
FIG. 10 is an exploded view of the needle guide of FIG. 4 where the structure upon which the pivot member is coupled is visible.

Now referring to FIG. 10, there is shown an exploded view of the present invention which shows the details of how pivoting member 406 pivots on the base 402, and further shows a resilient member 1002 which biases the pivoting member into a position of reduced size of said instrument gap.

Figure 11:
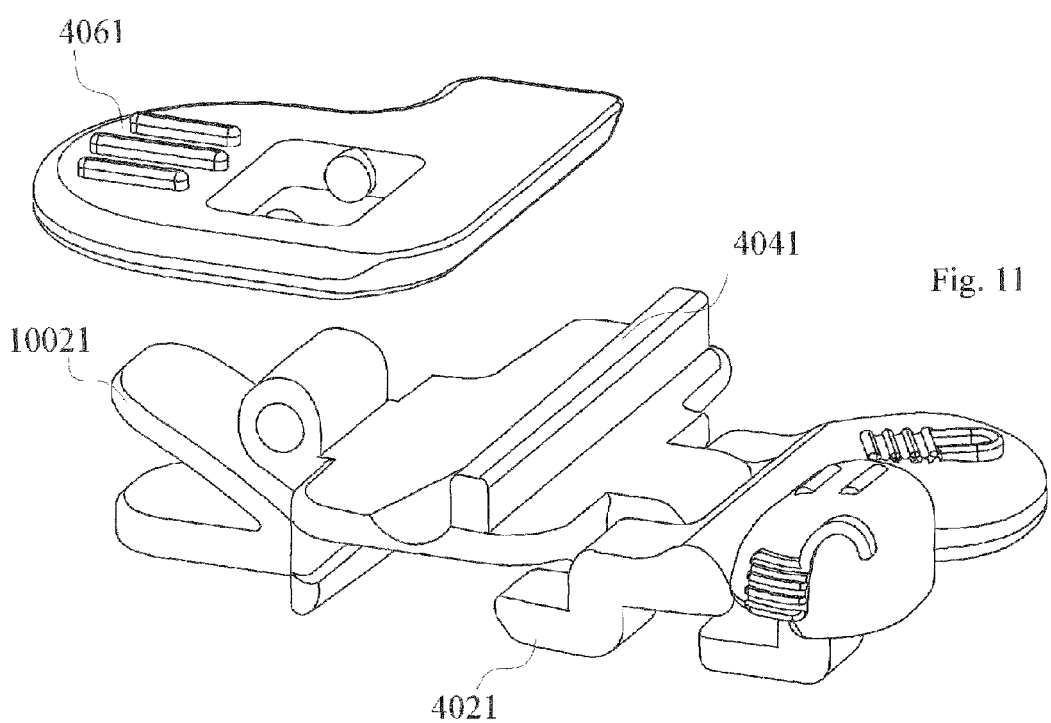
FIG. 11 is an exploded view of an alternate embodiment of the present invention.

Now referring to FIG. 11, there is shown an alternate embodiment of the present invention which shows differing ways to attach the invention to a medical device. The Base 4021 is shown as a push button locking and unlocking base for providing easy attachment of the invention to a bracket or medical device. It should be understood that base 402 and base 4021 are merely representative of the many ways that the present invention could be mounted to medical devices. It is intended that the present invention cover these various ways of attachment. Similarly, pivoting member 4061 is coupled to base 4021 in a slightly different way than base 402 and pivoting member 406. This, too, is representative of the many ways to make this pivoting type attachment. A key aspect of the invention is that the pivoting member 4061 pivots with respect to stationary rest 4041 and is biased into position by resilient member 10021.

Throughout this description, reference is made to a needle guide, because it is believed that the beneficial aspects of the present invention would be most readily apparent when used in connection with needle guides; however, it should be understood that the present invention is not intended to be limited to guiding needles, and should be hereby construed to include other medical instruments, catheters, tools, equipment and methodologies as well, where it is desirable to guide a needle.

Throughout this description, reference is made to a medical imaging system, because it is believed that the beneficial aspects of the present invention would be most readily apparent when used in connection with medical imaging; however, it should be understood that the present invention is not intended to be limited to imaging, and should be hereby construed to include other medical tools, equipment and methodologies as well, where it is desirable to guide a needle.

Throughout this document, references are made to "vertical" and "horizontal". These terms are intended to mean "substantially vertical" and "substantially horizontal". Minor deviations from vertical and minor deviations from horizontal are intended to be included therein. Also see the above definition on vertical axis 107.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

What is claimed is:

1. An improved medical instrument guiding apparatus for use with a medical imaging transceiver assembly, the medical instrument guiding apparatus comprising:

a medical imaging transceiver comprising a proximal handle end and a distal signal transmission end and an axis generally orthogonal with respect to said distal signal transmission end, which axis defines a transmission direction;

a base, comprising a back portion and a stationary stop which is disposed at said back portion, said base detachably coupled to said medical imaging transceiver between said handle end and said signal transmission end;

a pivoting member which is pivotable with respect to said base;

said stationary stop and said pivoting member are configured so as to define an instrument gap between said stationary stop and said pivoting member and further configured to permit removal of an instrument from said instrument gap by pulling said back portion of said base away from said instrument, through an enlarged instrument gap;

said stationary stop and said pivoting member further configured to define said instrument gap as a longitudinal instrument gap which is offset from the axis and angled with respect to the axis and the transmission direction; and said stationary stop and said pivoting member further configured to define a variably sized instrument gap which increases to accommodate larger diameter instruments when said pivoting member is pivoted.

2. The apparatus of claim 1 wherein said pivoting member comprises an instrument engaging face which is configured at an oblique angle with respect to said back portion, so that a differential in instrument gap width exists at differing distances from said back portion.

3. The apparatus of claim 2 wherein said stationary stop is orthogonal to said back portion.

4. The apparatus of claim 3 wherein said stationary stop is formed in a single piece of material with said back portion.

5. The apparatus of claim 4 wherein said pivoting member further comprises a proximal end and a distal end, and said proximal end comprises said instrument engaging face and said distal end comprises an actuation region.

6. The apparatus of claim 5 wherein said actuation region further comprises surface features configured to increase engagement of said actuation region during pivoting of said pivoting member.

7. The apparatus of claim 6 wherein said stationary stop has a beveled top edge configured to facilitate insertion of an instrument into said instrument gap from a location above said beveled top edge.

8. The apparatus of claim 7 further comprising a resilient member disposed between said pivoting member and said base so as to bias said pivoting member into a position which reduces said instrument gap.

9. The apparatus of claim 8 wherein said resilient member is a plastic spring formed into one of said base and said pivoting member.

10. The apparatus of claim 9 wherein said resilient member is formed into said base.

* * * * *